United States Patent [19]
Maunder et al.

[11] Patent Number: 5,955,057
[45] Date of Patent: Sep. 21, 1999

[54] EFFERVESCING OR FOAMING BATH SHAPE OR SOLID

[75] Inventors: Terry W. Maunder, Richmond; Robert B. Rieveley, Vancouver, both of Canada

[73] Assignee: Biotech Holdings Ltd., Vancouver, Canada

[21] Appl. No.: 09/096,517

[22] Filed: Jun. 12, 1998

[51] Int. Cl.$^6$ ....................................................... A61K 9/20
[52] U.S. Cl. .............................. 424/44; 424/43; 424/466; 510/447; 514/957
[58] Field of Search ................................ 424/44, 43, 466; 514/957

[56] References Cited

U.S. PATENT DOCUMENTS 4,666,707  5/1987  Eguchi et al. .............................. 424/44
5,110,603  5/1992  Rau ......................................... 424/466

*Primary Examiner*—Cecilia J. Tsang
*Attorney, Agent, or Firm*—Oyen Wiggs Green & Mutala

[57] ABSTRACT

This invention is directed to a novel effervescing foaming bath shape or solid composition. More particularly, this invention pertains to a novel effervescing or foaming bath ball composition which has rapid mixing and production time, and antiseptic and skin conditioning properties. A bath shape or sold formulation comprising: (a) between 40 to 90% by weight of sodium bicarbonate; (b) between 5 to 50% by weight of organic acid; and (c) between 0.5 to 15% weight of alcohol. The formulation can also include (d) between 0.5 to 10% of vegetable oil; (e) between about 0.01 to 0.1 % weight of FD&C certified color to provide a pleasing color to the formulation; (f) between about 0.01 to 10% weight of fragrance to provide an appealing aroma to the composition, and a surfactant.

34 Claims, No Drawings

EFFERVESCING OR FOAMING BATH SHAPE OR SOLID

FIELD OF THE INVENTION

This invention is directed to a novel effervescing or foaming bath shape or solid composition. More particularly, this invention pertains to a novel effervescing or foaming bath ball composition which has rapid mixing and drying qualities thereby resulting in shorter production time, as well as antiseptic and skin conditioning properties.

BACKGROUND OF THE INVENTION

In recent years, it has become very popular to add bath salts or bath balls to a bath. Generally, such bath salt and bath ball compositions contain an inorganic salt mixture comprising sodium sulfate, borax, sulfur, sodium chloride or a carbonate salt, together with perfume, colourant and plant extract. The purpose of the salts or balls is to provide the bath with perfume and/or colour, to improve the aesthetics of the bath and at the same time create a stimulating effect on the skin. In the case of effervescing salt compositions, they usually comprise a combination of a carbonate salt and an acid which when dissolved in the bath, produce carbon dioxide gas bubbles which provide a relaxing and refreshing sensation to the bath. In the case of foaming bath salts or balls, a surfactant is included.

Several U.S. patents disclose bath salt or bath ball compositions. U.S. Pat. No. 4,666,707, Eguchi et al., assigned to Kao Corporation, granted May 19, 1987, discloses a weakly acidic effervescing bath salt composition which contains a carbonate salt and an acid which gives the bath a weakly acidic character. The carbonate salt that is incorporated in the weakly acidic bath salt composition can be sodium hydrogen carbonate, sodium carbonate, sodium sesquicarbonate, potassium hydrogen carbonate, potassium carbonate, potassium sesquicarbonate, ammonium hydrogen carbonate, ammonium carbonate and ammonium sesquicarbonate. These salts may be used either alone or in combination with one another. The weakly acidic nature of the bath purportedly enhances retention of carbon dioxide gas in the bath which purportedly promotes blood circulation and prevents a chill after bathing. The composition also incorporates a moisturizer which allegedly leads to a synergistic increase in blood circulation and enhances moisture in the skin.

The acid contained in the weakly acidic bath salt composition purportedly can be an organic acid such as formic acid, a straight chain aliphatic acid, for example, acetic acid, propionic acid, butyric acid or valeric acid; dicarboxylic acid such as oxalic acid, malonic acid, succinic acid, glutaric acid, adipic acid, pimelio acid, fumaric acid, maleic acid, phthalic acid, isophthalic acid and terephthalic acid; acidic amino acids such as glutamic acid and aspartic acid; hydroxy acids such as glycolic acid, lactic acid, hydroxyacrylic acid, α-hydroxybutyric acid, glyceric acid, tartronic acid, malic acid, tartaric acid, hydroxybenzoic acid, citric acid, salicylic acid (o, m, p), gallic acid, mandelic acid, tropic acid, ascorbic acid and gluconic acid; cinnamic acid, benzoic acid, phenylacetic acid, nicotinic acid, kainic acid, sorbic acid, pyrrolidonecarboxylic acid, trimellitic acid, benzenesulfonic acid and toluenesulfonic acid; and acidic salts of these organic acids. The inorganic acids include, among others, phosphoric acid, potassium dihydrogen phosphate, sodium dihydrogen phosphate, sodium sulfite, potassium sulfite, sodium pyrosulfite (sodium metabisulfite), potassium pyrosulfite (potassium metabisulfite), acidic sodium hexametaphosphate, acidic potassium hexametaphosphate, acidic sodium pyrophosphate, acidic potassium pyrophosphate and sulfamic acid. Preferred acids are aliphatic dicarboxylic acids such as succinic acid, and fumaric acid and phosphoric acid as well as acidic salts of these.

Typical examples of the moisturizer that can purportedly be used in the composition are stated as follows:

(1) Organic acid salts such as sodium lactate, disodium tartrate, sodium pyrrolidonecarboxylate and disodium glutamate;

(2) Polyhydric alcohols such as propylene glycol, 1,3-butylene glycol, glycerol and sorbitol;

(3) Water-soluble macromolecules such as polyethylene glycol, polyvinyl alcohol, sodium alginate and polyvinylpyrrolidone;

(4) Mucopolysaccharides such as chondroitin sulfate and hyaluronic acid;

(5) Collagen and derivatives thereof; and (6) Nucleic acids (DNA, RNA), proteins such as elastin, keratin, fibroin, and hydrolyzates thereof.

The ratio between the carbonate salt and the acid in the bath salt composition is stated to be such that when added to the bath, the bath salt composition renders the bath weakly acidic, namely such that a 0.01 weight percent aqueous solution of the bath salt composition has a pH of 4 to 7, preferably 6.0 to 6.7. When the pH is lower than 4, the stimulation to the skin is said to become severe while at the same time there is a risk of corrosively damaging the bath heater and the like. At a pH exceeding 7, it is stated that the carbon dioxide retention and blood circulation promotion effects of the composition cannot be produced.

According to the inventors, Eguchi et al., the effect of the invention is based on the principle that, on the acidic side of a pH of 7.0, carbon dioxide occurs as the $CO_2$ molecule and produces the blood circulation promoting effect whereas on the alkaline side of a pH of 7.0, carbon dioxide occurs as the $CO_3^{2-}$ or $HCO_3^-$ ion, so that the blood circulation promoting effect cannot be produced. The proportion of carbonate salt to acid to satisfy the required conditions may vary depending on the kind of carbonate salt and of acid but, preferably, the carbonate salt allegedly accounts for 5 to 80% by weight, more preferably 10 to 50%, and the acid purportedly accounts for 10 to 80%, more preferably 15 to 50%, based on the whole composition. It is said that the moisturizer can be incorporated in an amount varying in a wide range. Generally, however, it is used in an amount of 0.001 to 10%, preferably 0.01 to 2%, on the whole composition basis.

Other effervescing bath preparations are also known. A fundamental preparation is disclosed in U.S. Pat. No. 4,650,667. A further example is a preparation which employs low-cost fumaric acid, and is available under the trademark AC-TIBATH®, as well as other names.

U.S. Pat. No. 5,110,603, Rau, assigned to Kao Corporation, and the Andrew Jergens Company, granted May 5, 1992, discloses a colloidal material containing bath composition which, when the composition is dissolved in water, also generates carbon dioxide. The composition is physically bound together as a tablet with a colloidal material. The effervescence produced by dissolving the tablet in the water purportedly improves dispersion of the colloidal material, and maintains the colloidal material in suspension in the water for a longer period of time. The colloidal material is selected so as to provide relief from skin irritation. An acid, a carbonate salt, and a colloidal material such as colloidal oatmeal may be tableted to provide an effective, easily stored and handled product. Specifically, the bath composition is stated to comprise aggregated particles composed of (1) a composition which will dissolve in warm and hot water to release carbon dioxide, the composition comprising a carbonate salt and an acid. The carbonate salt and acid are intimately mixed with 0.1–50%, by weight, of a colloidal material suitable or treatment of skin. The colloidal material is selected from the group consisting of colloidal oatmeal, flour derived from corn, wheat, soy, rice or barley, meals obtained from corn or almond, hydrophobic starch obtained from corn, wheat, rice, potato, water-insoluble gums, cellulose and mixtures thereof.

The treatment of minor skin irritations, and in particular, relief from itching induced by inflammation, disease, trauma and the like, through the water-mediated application of colloidal materials is well known. Prominent among various materials of this type is colloidal oatmeal, commercially available under the mark AVEENO® from S.C. Johnson Company, as well as from other sources. Hydrophobic starches are also well known in this application as substances which, when dispersed in water, settle on and desensitize the skin, and provide temporary relief. In general, the colloidal material treatments are effected by dispersing the colloidal material in bath water, and then bathing in the bath suspension. This method presents a number of problems.

Maximum effectiveness is stated to be achieved by thorough dispersion of the colloidal material throughout the bath water, as these materials are generally in powder form. There is an inherent problem because thorough dispersion of the material tends to be frustrated by the tendency of such materials to swell, soften and agglomerature upon exposure to water. A further problem is that agglomerated particles of this type tend to settle relatively rapidly, thereby reducing shelf life and effectiveness in the bath. Yet a further problem is that, due to the colloidal nature of this material, it tends to persist in the tub or bathing enclosure even after the water is drained. The problem is compounded because the greater the degree of agglomeration, the more difficult it is to remove residual material.

SUMMARY OF INVENTION

The invention in one embodiment is directed to a bath shape or solid formulation comprising: (a) between 40 to 90% by weight of sodium bicarbonate; (b) between 5 to 50% by weight of organic acid; and (c) between 0.5 to 15% weight of alcohol.

The formulation can include between 0.5 to 10% of animal, plant or mineral oil and between about 0.01 to 0.1% weight of FD&C certified colour to provide a pleasing colour to the formulation. The formulation can also include between about 0.01 to 10% weight of fragrance to provide an appealing aroma to the composition.

The organic acid can be selected from the group consisting of citric acid, ascorbic acid and acetic acid. The alcohol can be selected from the group consisting of methyl alcohol, ethyl alcohol, propyl alcohol and butyl alcohol. The alcohol can be hydrous alcohol. The oil can be selected from the group consisting of vegetable oil, canola oil, olive oil, safflower oil, sunflower seed oil, corn oil, nut oil, fruit oil, mineral oil, animal oil and lanolin.

The formulation can include between about 0.25 and 50% weight of sodium carbonate. It can also include a surfactant. The surfactant can be an alkanolamide or an N-alkylpyrrolidone.

The formulation can include between about 0.25 and 10% weight of lauramide diethanolamine, or between about 0.25 and 10% weight of lauryl pyrrolidone, or between about 0.5 to 10% weight of lauramide monoethanolamine.

The formulation can also include other suitable ingredients. The formulation in another embodiment may omit component (c), the alcohol, and include a moisturizer and a surfactant to provide a foaming quality to the formulation. The surfactant can be an alkanolamide or an N-alkylpyrrolidone, lauramide diethanolamine, lauryl pyrrolidon, or lauramide monoethanolamine.

The moisturizer can be selected from the group consisting of organic acid salts such as sodium lactate, disodium tartrate, sodium pyrrolidonecarboxylate and disodium glutamate, polyhydric alcohols such as propylene glycol, 1,3-butylene glycol, glycerol and sorbitol, water-soluble macromolecules such as polyethylene glycol, polyvinyl alcohol, sodium alginate and polyvinylpyrrolidone, mucopolysaccharides such as chondroitin sulfate and hyaluronic acid, collagen and derivatives thereof, and nucleic acids (DNA, RNA), proteins such as elastin, keratin, fibroin, and hydrolyzates thereof.

DETAILED DESCRIPTION OF SPECIFIC EMBODIMENTS OF THE INVENTION

We have invented novel effervescing or foaming bath shapes or solids which have hard even colour surfaces which provide superior appearance and effectiveness in the bath, and also have antiseptic and skin moisturizing properties. The shapes or solids can be in the form of balls, tablets, discs, flowers, or any other aesthetically pleasing shape. The novel effervescing or foaming bath shapes or solids formulations have the following generic formulation:

(a) sodium bicarbonate, 40 to 90% weight;

(b) organic acid such as citric acid, 5 to 50% weight; and (c) alcohol such as ethyl alcohol, methyl alcohol, propyl alcohol or butyl alcohol, 0.5 to 15% weight. Preferably, the alcohol is hydrous. A preferred hydrous alcohol is hydrous ethanol with 5% water.

This formulation mixes readily in about 1 to 2 minutes, whereas the prior art compositions which contain lubricants and moisturizers such as propylene glycol, for example, take about 10 minutes to mix. This dramatically reduces production time and reduces production cost. The hydrous alcohol enhances the mixing of the inorganic sodium bicarbonate and the organic acid.

A problem with prior art bath balls and salts compositions is that the moisturizers, such as propylene glycol, do not dry or evaporate and tend to leave a residue in the bath tub. Furthermore, the non-drying ingredients absorb the colour and tend under gravity to settle to the lower side of the bath ball. This detracts from the appearance of the bath ball, thereby reducing sales appeal. Also, sodium carbonate is not highly soluble in water and tends to deposit on the bath tub surfaces.

Also, in the prior art compositions, the moisturizers such as propylene glycol, when shipped via air or land, may tend to attract the colourant, and migrate to locations on the surface of the compositions. Thus the prior art compositions tend over time to develop unattractive blotchy or mottled surface characteristics. This also greatly reduces sales appeal. Also degraded compositions must be sold at reduced price or thrown away.

Notwithstanding that a moisturizer may not be desirable in most formulations, nonetheless, in certain embodiments incorporating a surfactant, a moisturizer may be desirable.

Such formulations in their simplest aspect, comprise sodium bicarbonate, organic acid, a moisturizer and a surfactant. The moisturizer can be any one or more of organic acid salts such as sodium lactate, disodium tartrate, sodium pyrrolidonecarboxylate and disodium glutamate, polyhydric alcohols such as propylene glycol, 1,3-butylene glycol, glycerol and sorbitol, water-soluble macromolecules such as polyethylene glycol, polyvinyl alcohol, sodium alginate and polyvinylpyrrolidone, mucopolysaccharides such as chondroitin sulfate and hyaluronic acid, collagen and derivatives thereof, and nucleic acids (DNA, RNA), proteins such as elastin, keratin, fibroin, and hydrolyzates thereof.

As mentioned, an important characteristic of the invention is that the formulations of the invention mix quickly (thereby reducing production time) and dry quickly to produce a shape or solid that has uniform colour throughout, a smooth, hard non-powdery surface, a good shelf life, and adapts to the use of both strong and pastel colours, without fear of spotting or blotching developing during shipment or while displayed on the shelves of sales outlets. Moreover, in the basic formulation, sufficient alcohol remains in the interior of the finished shape or solid that mild antiseptic quality is provided to the bath water, when the formulation is dissolved in the bath. This is important because a bath should be hygienic since delicate private body parts of the bather are exposed to the bath water.

In addition, the formulation can include:
(d) animal oil such as lanolin, mineral oil or vegetable oil such as canola oil (oil obtained from canola seed), safflower oil, sunflower seed oil, olive oil, corn oil, nut oil and fruit oil, and the like, 0.5 to 10% weight.

The formulation can also include appropriate amounts of:
(e) FD&C certified colours to import colour to the formulation; and
(f) fragrance.

As an additional ingredient of the foregoing basic formulation comprising compounds (a), (b) and (c), sodium carbonate can be included in the range 0.25 to 50% weight in order to provide more alkalinity to the formulation. Sodium carbonate (soda ash) is an odourless hydroscopic powder. It combines with water and evolves heat. It renders an aqueous medium slightly alkaline in character. Sodium carbonate has been used in the treatment of eczema, to cleanse skin and as a water softener.

To create a foaming quality to the basic formulation comprising components (a), (b) and (c), or (a) and (b) alone, a suitable surfactant can be included. Such surfactant can be a non-ionic, anionic, or cationic surfactant. However, preferred surfactants are suitable alkanolamides or N-alkylpyrrolidones, such as lauramide diethanolamine, lauramide monoethanolamine and lauryl pyrrolidone. These can be added in the range 0.25 to 10% weight. These latter surfactants have emulsifier, dispersing and wetting agent properties and are formulated from combinations of lauric acid (dodecenoic acid), diethanolamine, monoethanolamine and pyrrolidone. Lauric acid ($C_{12}H_{24}O_2$) is a saturated fatty acid. Monoethanolamine and diethanolamine are mild pharmaceutic aids and are frequently used in cosmetics and pharmaceuticals. Diethanolamine has humectant and softening agent properties. The alkanolamides and N-alkylpyrrolidones are particularly compatible with the other ingredients in the formulation.

In another embodiment, the formulation can comprise components (a) and (b) above, together with a suitable surfactant, such as the surfactants mentioned above, as well as a moisturizer as described above. This formulation omits the hydrous alcohol.

Sodium bicarbonate, which is a component of the basic generic formulation, comprising components (a), (b) and (c) when dissolved in water, decomposes into carbon dioxide bubbles and a small amount of sodium carbonate. The sodium bicarbonate generates an alkaline quality to the water, such alkalinity increasing with water temperature. This promotes skin cleansing.

The organic acid such as citric acid, or other organic acid, is used along with the sodium bicarbonate, or sodium carbonate if present, to control the overall pH of the bath ball formulation when dissolved in water, so that it is in the range between about 6.8 to about 7.2 pH.

The alcohol is preferably ethyl alcohol, but methyl alcohol, propyl alcohol, isopropyl alcohol, or butyl alcohol are also suitable. The alcohol preferably should be hydrous alcohol because the small amount of water present, usually about 5% wt., seems to have a catalytic quality and enables the basic components of the formulation to mix readily and rapidly compared to prior art compositions. The alcohol provides an antiseptic quality to the basic bath shape or solid formulation, and assists in binding the components together. The alcohol also dries rapidly from the surface of the basic shape or solid and thus provides a harder smoother surface.

The oil, such as a plant oil like vegetable oil, canola oil, safflower oil, sunflower seed oil, corn oil, nut oil, fruit oil, olive oil, mineral oil, or animal oil such as lanolin, lends a pleasant smooth lubricational quality to the formulation and provides a superior surface to the finished shape or solid.

The alkanolamide or N-alkylpyrrolidone surfactant such as lauramide diethanolamine, lauryl pyrrolidine, or lauramide monoethanolamine, serve as detergents and enable the overall formulation, containing both inorganic and organic components, to be compatible with one another in the solid form, and to dissolve readily in bath water without creating cloudiness or a general unappealing character to the bath water.

The FD&C certified colours can be blue, purple, turquoise, green, or other acceptable colours which impart a pleasing colour quality to the solid bath ball, and also to the bath water when dissolved in the bath water. The basic formulation is highly compatible with both strong primary colour FD&C certified colours, as well as pastel colours. Sufficient colour is added to provide an appealing colour to the shape or solid, as well as to the bath, when the shape or solid is dissolved in the bath. Furthermore, since no particular ingredient in the basic formulation is more attractive to the FD&C certified colour than another, the shape or solid maintains an even, smooth colour for a long period of time, regardless of shipping or storage at high temperatures.

The fragrance can be selected from a suitable amount of a wide range of natural or synthetic flavours such as fruit flavours, for example, cherry, apple, strawberry, lemon, blueberry, raspberry, peach, apricot, mango, guava, kiwi, or natural vegetable fragrances such as balsam, herbs, aloe vera, or flower fragrances such as rose, apple blossom, orange blossom, magnolia blossom, gardenia blossom, and the like.

The following Table 1 tabulates the acceptable component ranges for four specific bath shapes or solids formulations:

TABLE 1

| Component | Weight Range (%) | | | |
| --- | --- | --- | --- | --- |
| | #1 | #2 | #3 | #4 |
| Sodium bicarbonate | 40–90% | 40–90% | 40–90% | 40–90% |
| Sodium carbonate | 0.25–50% | — | — | — |
| Citric acid or other acid | 5–50% | 5–50% | 5–50% | 5–50% |
| Alcohol | 0.5–15% | 0.5–15% | 0.5–15% | 0.5–15% |
| Canola oil or other oil | 0.5–10% | 0.5–10% | 0.5–10% | 0.5–10% |
| Lauramide DEA | — | 0.25–10% | — | — |
| Lauryl Pyrrolidone | — | — | 0.25–10% | — |
| Lauramide MEA | — | — | — | 0.25–10% |
| FD&C certified colours | (small acceptable quantity) | | | |
| Fragrance | (small acceptable quantity) | | | |

The following specific formulations have been prepared and the ingredients have been demonstrated to be compatible with one another when mixed together and in finished solid form with good shelf life and highly pleasing appearance. They have been tested in warm and hot bath water and demonstrated to dissolve readily and provide a strong bubble generating, and non-cloud or oil creating effect.

| | Formula % wt. |
| --- | --- |
| Example 1 | |
| Formulation for Regular Bath Ball-Basic | |
| Sodium bicarbonate | 74.00 |
| Sodium carbonate | 1.50 |
| Citric Acid or other acid | 20.00 |
| Alcohol | 2.41 |
| Canola oil or other oil | 1.50 |
| FD&C certified colours | 0.09 |
| Fragrance | 0.50 |
| TOTAL | 100.00 |
| Example 2 | |
| Foaming Ball Formulation-#1 | |
| Sodium bicarbonate | 73.71 |
| Citric Acid or other acid | 21.50 |
| Alcohol | 1.70 |
| Canola oil or other oil | 1.50 |
| Lauramide DEA | 1.00 |
| FD&C certified colours | 0.09 |
| Fragrance | 0.50 |
| TOTAL | 100.00 |
| Example 3 | |
| Foaming Ball Formulation-#2 | |
| Sodium bicarbonate | 73.71 |
| Citric Acid or other acid | 21.50 |
| Alcohol | 1.70 |
| Canola oil or other oil | 1.50 |
| Lauryl Pyrrolidone | 1.00 |
| FD&C certified colours | 0.09 |
| Fragrance | 0.50 |
| TOTAL | 100.00 |
| Example 4 | |
| Foaming Ball Formulation-#3 | |
| Sodium bicarbonate | 73.71 |
| Citric Acid or other acid | 21.50 |
| Alcohol | 1.70 |
| Canola oil or other oil | 1.50 |
| Lauramide MEA | 1.00 |
| FD&C certified colours | 0.09 |
| Fragrance | 0.50 |
| TOTAL | 100.00 |

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A dry, solid, antisptic, bath shape or formulation for dissolving in a bath consisting essentially of:
   (a) between 40 to 90% by weight of sodium bicarbonate;
   (b) between 5 to 50% by weight of organic acid; and
   (c) between 0.5 to 15% weight of alcohol, the formulation being mixed and formed into a dry, solid, hard surface shape, suitable for dissolving in a bath of a human being.

2. A formulation as claimed in claim 1 further comprising between 0.5 to 10% of an oil.

3. A formulation as claimed in claim 1 further comprising between about 00.01 to 0.1% weight of FD&C certified colour to provide a pleasing colour to the formulation.

4. A formulation as claimed in claim 1 further comprising between about 0.01 to 10% weight of fragrance to provide an appealing aroma to the composition.

5. A formulation as claimed in claim 1 wherein the organic acid is selected from the group consisting of citric acid, ascorbic acid and acetic acid.

6. A formulation as claimed in claim 1 wherein the organic acid is citric acid.

7. A formulation as claimed in claim 2 wherein the organic acid is selected from the group consisting of citric acid, ascorbic acid and acetic acid.

8. A formulation as claimed in claim 2 wherein the organic acid is citric acid.

9. A formulation as claimed in claim 1 wherein the alcohol is selected from the group consisting of methyl alcohol, ethyl alcohol, propyl alcohol and butyl alcohol.

10. A formulation as claimed in claim 1 wherein the alcohol is ethyl alcohol.

11. A formulation as claimed in claim 9 wherein the alcohol is hydrous alcohol.

12. A formulation as claimed in claim 2 wherein the alcohol is selected from the group consisting of methyl alcohol, ethyl alcohol, propyl alcohol and butyl alcohol.

13. A formulation as claimed in claim 2 wherein the alcohol is ethyl alcohol.

14. A formulation as claimed in claim 12 wherein the alcohol is hydrous alcohol.

15. A formulation as claimed in claim 2 wherein the oil is selected from the group consisting of canola oil, olive oil, safflower oil, sunflower seed oil, corn oil, nut oil, fruit oil, mineral oil and animal oil.

16. A formulation as claimed in claim 2 wherein the oil is canola oil.

17. A formulation as claimed in claim 1 further comprising between about 0.25 and 50% weight of sodium carbonate.

18. A formulation as claimed in claim 1 further comprising a surfactant.

19. A formulation as claimed in claim 18 wherein the surfactant is an alkanolamide or an N-alkylpyrrolidone.

20. A formulation as claimed in claim 2 further comprising an alkanolamide or an N-alkylpyrrolidone.

21. A formulation as claimed in claim 1 further comprising between about 0.25 and 10% weight of lauramide diethanolamine.

22. A formulation as claimed in claim 1 further comprising between about 0.25 and 10% weight of lauryl pyrrolidone.

23. A formulation as claimed in claim 1 further comprising between about 0.5 to 10% weight of lauramide monoethanolamine.

24. A formulation as claimed in claim 1 further comprising other suitable bath cleanser and bath moisturizer ingredients.

25. A dry, solid, antiseptic bath shape consisting essentially of:
   (a) between 40 to 90% by weight of sodium bicarbonate;
   (b) between 5 to 50% by weight of organic acid; and
   including a moisturizer and a surfactant.

26. A formulation as claimed in claim 25 wherein the surfactant is an alkanolamide or an N-alkylpyrrolidone.

27. A formulation as claimed in claim 25 wherein the surfactant is lauramide diethanolamine.

28. A formulation as claimed in claim 25 wherein the surfactant is lauryl pyrrolidone.

29. A formulation as claimed in claim 25 wherein the surfactant is lauramide monoethanolamine.

30. A formulation as claimed in claim 25 wherein the moisturizer is one or more of an organic acid salt, sodium lactate, disodium tartrate, sodium pyrrolidonecarboxylate and disodium glutamate, polyhydric alcohol, propylene glycol, 1,3-butylene glycol, glycerol and sorbitol, a water-soluble macromolecule, polyethylene glycol, polyvinyl alcohol, sodium alginate and polyvinylpyrrolidone, mucopolysaccharide, chondroitin sulfate and hyaluronic acid, collagen and derivatives thereof, and nucleic acids (DNA, RNA), protein, elastin, keratin, fibroin, and hydrolyzates thereof.

31. A formulation as claimed in claim 26 wherein the moisturizer is one or more of an organic acid salt, sodium lactate, disodium tartrate, sodium pyrrolidonecarboxylate and disodium glutamate, polyhydric alcohol, propylene glycol, 1,3-butylene glycol, glycerol and sorbitol, a water-soluble macromolecule, polyethylene glycol, polyvinyl alcohol, sodium alginate and polyvinylpyrrolidone, mucopolysaccharide, chondroitin sulfate and hyaluronic acid, collagen and derivatives thereof, and nucleic acids (DNA, RNA), protein, elastin, keratin, fibroin, and hydrolyzates thereof.

32. A formulation as claimed in claim 1 wherein the formulation when dissolved in bath water causes the bath water to have an overall pH of between about 6.8 to about 7.2.

33. A dry, solid, antiseptic bath ball having the formula:
   (a) sodium bicarbonate—74% weight;
   (b) sodium carbonate—1.5% weight;
   (c) citric acid—20% weight;
   (d) alcohol—2.4% weight;
   (e) canola oil—1.5% weight;
   (f) FD&C certified colours—0.09% weight
   (g) fragrance—0.5% weight.

34. A dry, solid, antiseptic bath ball having the formula:
   (a) sodium bicarbonate—73.71% weight;
   (b) citric acid or other organic acid—21.50% weight;
   (c) alcohol—1.7% weight;
   (d) canola oil or other oil—1.5% weight;
   (e) lauramide DEA, lauryl pyrrolidone or lauramide MEA—1.00% weight
   (f) FD&C certified colours—0.09T weight
   (g) fragrance—0.5% weight.

* * * * *